United States Patent
Keller

(10) Patent No.: US 11,854,687 B2
(45) Date of Patent: *Dec. 26, 2023

(54) BEDSIDE INTERFACE FOR PERCUTANEOUS CORONARY INTERVENTION PLANNING

(71) Applicant: PHILIPS IMAGE GUIDED THERAPY CORPORATION, San Diego, CA (US)

(72) Inventor: Jacqueline Keller, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 143 days.

This patent is subject to a terminal disclaimer.

(21) Appl. No.: 16/881,049

(22) Filed: May 22, 2020

(65) Prior Publication Data
US 2020/0281748 A1 Sep. 10, 2020

Related U.S. Application Data

(63) Continuation of application No. 14/961,541, filed on Dec. 7, 2015, now Pat. No. 10,660,769.
(Continued)

(51) Int. Cl.
*A61B 5/02* (2006.01)
*G16H 30/40* (2018.01)
(Continued)

(52) U.S. Cl.
CPC ........... *G16H 30/40* (2018.01); *A61B 5/0035* (2013.01); *A61B 5/0066* (2013.01);
(Continued)

(58) Field of Classification Search
CPC ... A61B 5/02007; A61B 5/7264; A61B 5/743; A61B 6/032; A61B 8/12; A61B 8/5223; A61B 5/055; A61B 5/6852; G16H 40/63
See application file for complete search history.

(56) References Cited

U.S. PATENT DOCUMENTS 8,754,865 B2 6/2014 Merritt
9,339,348 B2 5/2016 Davies
(Continued)

FOREIGN PATENT DOCUMENTS

WO 2013028612 A1 2/2013

OTHER PUBLICATIONS

"Operator's Manual: for use with Volcano Imaging and Pressure Systems", Apr. 2014, pp. 1-64.

*Primary Examiner* — Rochelle D Turchen

(57) ABSTRACT

Devices, systems, and methods configured to assess the severity of a blockage in a vessel and, in particular, a stenosis in a blood vessel, provide measurements of a vessel that allow assessment of the vessel and, in particular, any stenosis or lesion of the vessel, simulate diagnostic visualizations a first visualization device and a second visualization device. For example, the methods can include displaying, on a first visualization device, an image of the vessel with treatment diagnostic visualizations based on obtained pressure measurements and displaying, on a second visualization device, a portion of the image of the vessel with diagnostic visualizations based on the obtained pressure measurements, wherein the portion of the image of the vessel displayed on the second visualization device is a close up of a region of interest of the vessel.

12 Claims, 10 Drawing Sheets

Related U.S. Application Data

(60) Provisional application No. 62/089,051, filed on Dec. 8, 2014.

(51) Int. Cl.

| | |
|---|---|
| *A61B 5/0215* | (2006.01) |
| *A61B 5/00* | (2006.01) |
| *A61B 6/00* | (2006.01) |
| *A61B 6/03* | (2006.01) |
| *A61B 8/12* | (2006.01) |
| *A61B 8/08* | (2006.01) |
| *A61F 2/82* | (2013.01) |
| *A61B 6/12* | (2006.01) |
| *A61B 8/06* | (2006.01) |
| *A61B 34/10* | (2016.01) |
| *G06F 3/0488* | (2022.01) |
| *G16H 30/20* | (2018.01) |
| *G16H 40/63* | (2018.01) |
| *G16H 50/50* | (2018.01) |
| *G06F 3/04815* | (2022.01) |
| *A61B 5/055* | (2006.01) |

(52) U.S. Cl.
CPC ........ *A61B 5/02007* (2013.01); *A61B 5/0215* (2013.01); *A61B 5/6876* (2013.01); *A61B 5/7264* (2013.01); *A61B 5/743* (2013.01); *A61B 6/032* (2013.01); *A61B 6/12* (2013.01); *A61B 6/461* (2013.01); *A61B 6/469* (2013.01); *A61B 6/504* (2013.01); *A61B 8/06* (2013.01); *A61B 8/0891* (2013.01); *A61B 8/12* (2013.01); *A61B 8/5223* (2013.01); *A61B 34/10* (2016.02); *A61F 2/82* (2013.01); *G06F 3/0488* (2013.01); *G06F 3/04815* (2013.01); *G16H 30/20* (2018.01); *G16H 40/63* (2018.01); *G16H 50/50* (2018.01); *A61B 5/004* (2013.01); *A61B 5/0084* (2013.01); *A61B 5/02158* (2013.01); *A61B 5/055* (2013.01); *A61B 5/6852* (2013.01); *A61B 5/7445* (2013.01); *A61B 2034/101* (2016.02); *A61B 2034/107* (2016.02)

(56) References Cited

U.S. PATENT DOCUMENTS

| | | |
|---|---|---|
| 2013/0072784 A1 | 3/2013 | Velusamy |
| 2013/0120297 A1 | 5/2013 | Merritt |
| 2013/0279723 A1 | 10/2013 | Hooley |
| 2014/0046642 A1 | 2/2014 | Hart |
| 2014/0081140 A1 | 3/2014 | Kim |
| 2014/0100451 A1 | 4/2014 | Tolkowsky |
| 2014/0164969 A1* | 6/2014 | Hart .................. A61B 5/7425 715/771 |
| 2014/0187920 A1 | 7/2014 | Millett |
| 2014/0188503 A1 | 7/2014 | Balignasay |
| 2015/0119705 A1 | 4/2015 | Tochterman |
| 2015/0230713 A1 | 8/2015 | Merritt |
| 2015/0238096 A1 | 8/2015 | Merritt |
| 2016/0007866 A1 | 1/2016 | Tochterman |
| 2016/0066862 A1 | 3/2016 | Taylor |

* cited by examiner

BEDSIDE INTERFACE FOR PERCUTANEOUS CORONARY INTERVENTION PLANNING

CROSS REFERENCE TO RELATED APPLICATIONS

The present application is a continuation of U.S. application Ser. No. 14/961,541, filed Dec. 7, 2015, now U.S. Pat. No. 10,660,769, which claims priority to and the benefit of the U.S. Provisional Patent Application No. 62/089,051, filed Dec. 8, 2014, each of which is hereby incorporated by reference in its entirety.

TECHNICAL FIELD

The present disclosure relates generally to the assessment of vessels using a bedside interface. For example, some embodiments of the present disclosure are suited for assessing the severity of a blockage or other restriction to the flow of fluid through a vessel, such as a stenosis of a human blood vessel, by analyzing medical sensing data collected from the vessel using a touch-sensitive display of the bedside interface for use in percutaneous coronary intervention (PCI) planning.

BACKGROUND

Innovations in diagnosing and verifying the level of success of treatment of disease have progressed from solely external imaging processes to include internal diagnostic processes. In addition to traditional external image techniques such as X-ray, MRI, CT scans, fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy. Traditionally, many of these procedures are carried out by a multitude of physicians and clinicians, where each performs an assigned task. For example, a physician may stand next to a patient in the sterile field and guide the insertion and pull back of a medical sensing catheter. A clinician near the physician may control the procedure workflow with an interface, for example by starting and stopping the acquisition of medical data. Further, once medical data has been acquired, a second clinician in an adjacent control room working at a desktop computer may analyze the data, such as by reviewing quantities calculated from the acquired data. If a display is available in the sterile field, it is static and a physician may need to look at several images in succession. Also, the physician in the catheter lab and the clinician in the control room must communicate in order to acquire and analyze the relevant medical data. This may lengthen the time of the procedure, increase the cost of the procedure, and may lead to errors due to miscommunication or clinician inexperience.

One exemplary type of procedure involves pressure measurements within a blood vessel. A currently accepted technique for assessing the severity of a stenosis in the blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. There also remains a need for improved devices, systems, and methods for providing visual depictions of vessel that allow assessment of the vessel and, in particular, any stenosis or lesion of the vessel. Further, there remains a need for assessing the severity of a stenosis and for providing visual depictions of the vessel in an efficient and user friendly manner to facilitate PCI planning.

SUMMARY

Embodiments of the present disclosure are configured to assess the severity of a blockage in a vessel and, in particular, a stenosis in a blood vessel, provide visual depictions of vessel that allow assessment of the vessel and, in particular, any stenosis or lesion of the vessel, and simulate one or more treatment options for the vessel to facilitate planning and execution of percutaneous coronary interventions.

In some embodiments, methods of planning the treatment of a vessel of a patient are provided. These comprise obtaining pressure measurements from first and second instruments positioned within a vessel of a patient during a diagnostic procedure where the second instrument is moved longitudinally through the vessel from a first position to a second position and the first instrument remains stationary within the vessel; displaying on a first visualization device an image of the vessel with treatment diagnostic visualizations based on the obtained pressure measurements; and displaying on a second visualization device a portion of the image of the vessel with diagnostic visualizations based on the obtained pressure measurements, wherein the portion of the image of the vessel displayed on the second visualization device is a close up of a region of interest of the vessel.

In some embodiments, the first and second visualization devices are utilized to guide placement of one or more treatment devices associated with the identified treatment option. The second visualization device may also comprise a touch screen. The image displayed on the second visualization device may be at a higher magnification than the image displayed on the first visualization device. The second visualization device may be capable of higher magnification than the first visualization device.

In some instances, the image of the vessel comprises an extravascular image, and may be at least one of a two dimensional angiographic image, a three dimensional angiographic image, and a computed tomography angiographic (CTA) image. Alternatively, the image of the vessel comprises an intravascular image and may be at least one of an intravascular ultrasound (IVUS) image and an optical coherence tomography (OCT) image.

The diagnostic visualizations may include at least one of pressure measurements from the first instrument, pressure measurements from the second instrument, a ratio of the pressure measurements from the first and second instruments, an FFR value, or an iFR value. Additionally, the diagnostic visualizations may include an intensity map based on changes in a pressure ratio of the obtained pressure measurements from the first and second instruments, or a graph of a gradient of a pressure ratio of the obtained pressure measurements from the first and second instruments.

In one embodiment, a first treatment option is simulated, wherein simulating the first treatment option includes modifying the diagnostic visualizations based on an expected result of the first treatment option. Additionally, a second treatment option may be simulated, wherein simulating the second treatment option includes modifying the diagnostic visualizations based on an expected result of the second treatment option; and comparing the modified diagnostic visualizations associated with the first and second treatment options to identify a recommended treatment option. The first and second treatment options may be selected from the group consisting of performing angioplasty, deploying one or more stents, applying a pharmaceutical agent, or combinations thereof.

A system of planning the treatment of a vessel of a patient is also provided, comprising: a first instrument sized and shaped for introduction into the vessel of the patient; a second instrument sized and shaped for introduction into the vessel of the patient; a processing system in communication with the first and second instruments, the processing unit configured to: obtain pressure measurements from first and second instruments positioned within a vessel of a patient during a diagnostic procedure where the second instrument is moved longitudinally through the vessel from a first position to a second position and the first instrument remains stationary within the vessel; display on a first visualization device an image of the vessel with treatment diagnostic visualizations based on the obtained pressure measurements; and display on a second visualization device a portion of the image of the vessel with diagnostic visualizations based on the obtained pressure measurements, wherein the portion of the image of the vessel displayed on the second visualization device is a close up of a region of interest of the vessel.

In some embodiments, the first and second visualization devices are utilized to guide placement of one or more treatment devices associated with the identified treatment option. The second visualization device may also comprise a touch screen. The image displayed on the second visualization device may be at a higher magnification than the image displayed on the first visualization device. The second visualization device may be capable of higher magnification than the first visualization device.

In some instances, the image of the vessel comprises an extravascular image, and may be at least one of a two dimensional angiographic image, a three dimensional angiographic image, and a computed tomography angiographic (CTA) image. Alternatively, the image of the vessel comprises an intravascular image and may be at least one of an intravascular ultrasound (IVUS) image and an optical coherence tomography (OCT) image.

The diagnostic visualizations may include at least one of pressure measurements from the first instrument, pressure measurements from the second instrument, a ratio of the pressure measurements from the first and second instruments, an FFR value, or an iFR value. Additionally, the diagnostic visualizations may include an intensity map based on changes in a pressure ratio of the obtained pressure measurements from the first and second instruments, or a graph of a gradient of a pressure ratio of the obtained pressure measurements from the first and second instruments.

In one embodiment, a first treatment option is simulated, wherein simulating the first treatment option includes modifying the diagnostic visualizations based on an expected result of the first treatment option. Additionally, a second treatment option may be simulated, wherein simulating the second treatment option includes modifying the diagnostic visualizations based on an expected result of the second treatment option; and comparing the modified diagnostic visualizations associated with the first and second treatment options to identify a recommended treatment option. The first and second treatment options may be selected from the group consisting of performing angioplasty, deploying one or more stents, applying a pharmaceutical agent, or combinations thereof.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
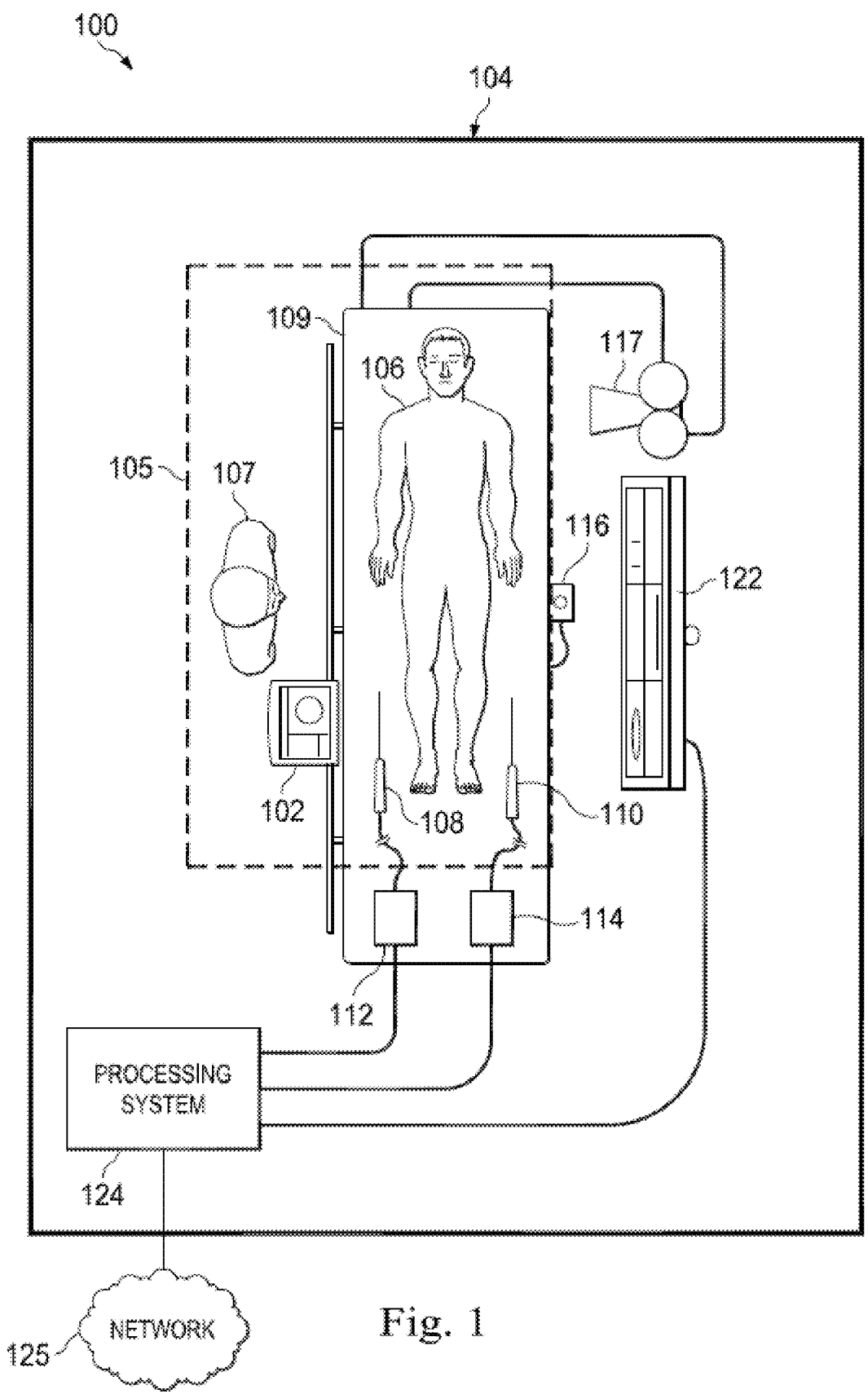
FIG. 1 is a schematic drawing depicting a medical sensing system including a bedside interface according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical sensing system 100 including a bedside interface 102 according to one embodiment of the present disclosure. In general, the medical sensing system 100 provides for coherent integration and consolidation of multiple forms of acquisition and processing elements designed to be sensitive to a variety of methods used to acquire and interpret human biological physiology and morphological information. More specifically, in system 100, the bedside interface 102 is a touch-enabled, integrated computing device for the acquisition, control, interpretation, measurement, and display of medical sensing data. In the illustrated embodiment, the bedside interface 102 is a tablet-style touch-sensitive computer that provides user controls and diagnostic images on a single surface. In the medical sensing system 100, the bedside interface 102 is operable to diagnostic visualizations and patient image data via graphical user interfaces (GUIs) corresponding to a plurality of medical sensing modalities. Among these options is the ability of the bedside interface 102 to present magnified images of trouble spots and provide greater levels of detail to a user. The bedside interface 102 will be described in greater detail in association with FIGS. 3-6.

In the illustrated embodiment, the medical sensing system 100 is deployed in a catheter lab 104. The catheter lab 104 may be used to perform on a patient 106 any number of medical sensing procedures alone or in combination such as, by way of example and not limitation, angiography, intravascular ultrasound (IVUS), virtual histology (VH), forward looking IVUS (FL-IVUS), intravascular photoacoustic (IVPA) imaging, pressure, fractional flow reserve (FFR) determination, flow velocity, flow volume, coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Catheter lab 104 can also conduct medical sensing procedures associated with Instant Wave-Free Ratio™ Functionality (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," hereby incorporated by reference in its entirety, which discloses the use of pressure ratios that are available without application of a hyperemic agent. Further, medical sensing procedures associated with compensated Pd/Pa ratios suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety, can be conducted in the catheter lab 104. In addition to controlling medical sensing systems, the bedside interface may be used to cooperate with and control medical treatment systems such as, for example but without limitation, those used for stent placement, coil embolism, ablation therapy, kidney stone treatments, basket placement in a cystoscopy, tumor removal, and chemical therapies. The catheter lab 104 further includes a sterile field 105 that encompasses the portions of the catheter lab surrounding the patient 106 on a procedure table 109 and a clinician 107, who may perform any number of medical sensing procedures or treatments.

As shown in FIG. 1, the bedside interface 102 may be positioned within the sterile field 105 and may be utilized by the clinician 107 to control a workflow of a medical sensing procedure or treatment being performed on the patient 106. For example, the clinician 107 may initiate the procedure workflow, watch real-time medical sensing data, such as pressure measurements (e.g., visual representations of pressure data, such as pressure waveforms), obtained during the procedure, and interact with the obtained medical sensing data using the bedside interface 102 inside of the sterile field 105. Additionally, the bedside interface may be used in conjunction with other imaging tools such as boom display 122. The bedside interface 102 and boom display 122 may display the same imagery, or the bedside interface 102 may provide alternative imagery to assist medical professionals in diagnosing a patient or performing surgery. For example, the bedside interface 102 may show an alternative view angle or may overlay a highlighted image on that shown on the boom display 122. In addition, the bedside interface 102 may be used to provide additional details on specific areas of interest. For example, the clinician 107 may view general diagnostic imagery on the boom display 122 and select a smaller portion of the imagery to display on the bedside interface 102. The magnification of the display on the bedside interface 102 may be variable, allowing the clinician to zoom in on particular areas while still keeping the general imagery in view on the boom display 122. The clinician 107 may zoom, rotate, and otherwise manipulate such images on the bedside interface 102 using simultaneous touch inputs (i.e. multitouch) and gestures. In alternative embodiments, the bedside interface 102 may be utilized outside of the sterile field 105, for instance, in other locations within the catheter lab 104 or in a control room adjacent to the catheter lab 104.

In the embodiment illustrated in FIG. 1, the medical sensing system 100 additionally includes a number of interconnected medical sensing-related tools in the catheter lab 104 to facilitate a pressure-sensing workflow procedure, such as a medical sensing device 108 and a medical sensing device 110, and a processing system 124. The medical sensing devices 108 and 110 can include pressure monitoring elements. Some embodiments of the medical sensing system 100 can include an patient interface module (PIM) 112 communicatively coupled to the medical sensing device 108, PIM 114 communicatively coupled to the medical sensing device 110, an electrocardiogram (ECG) device 116, an angiogram system 117, and a boom display 122. The bedside interface 102, PIMs 112 and 114, ECG device 116, angiography system 117, and boom display 122 are communicatively coupled to the processing system 124. In some embodiments, the medical sensing devices 108 and 110 can include imaging elements to facilitate an imaging workflow. In one embodiment, the processing system 124 is a computer workstation with the hardware and software to acquire, process, and display medical sensing data, but in other embodiments, the processing system may be any other type of computing system operable to process medical sensing data. For example, during a pressure-sensing workflow, the processing system 124 is operable to accept raw pressure data from the medical sensing devices 108 and 110 and/or the PIMs 112 and 114, transform the pressure data into screen displays including, e.g., visual representations such as pressure waveforms, numerical values, computed values, etc., and make the screen display available to the bedside interface 124, so that they may be displayed to the clinician 107 for analysis. In the embodiments in which the processing system 124 is a computer workstation, the system includes at least a processor such as a microinterface or a dedicated central processing unit (CPU), a non-transitory computer-readable storage medium such as a hard drive, random access memory (RAM), and/or compact disk read only memory (CD-ROM), a video interface such as a graphics processing unit (GPU), and a network communication device such as an Ethernet interface.

Further, the processing system 124 is communicatively coupled to a data network 125. In the illustrated embodiment, the data network 125 is a TCP/IP-based local area network (LAN); however in other embodiments, it may utilize a different protocol such as Synchronous Optical Networking (SONET), or may be a wide area network (WAN). In that regard, the network 125 may utilize wired and/or wireless connections. In some instances, at least a portion of the network 125 is a cellular network. Other components of the system 100, such as the bedside interface 102 and the boom display 122, are connected to the processing system 124 either directly through a wired or wireless interface, or indirectly via network 125 or other networking components. Further, the processing system 124 may connect to various resources via the network 125, such as a Digital Imaging and Communications in Medicine (DICOM) system, a Picture Archiving and Communication System (PACS), and a Hospital Information System. The processing system 124 can be similar to a multi-modality processing system that processes medical sensing data disclosed in U.S. Pat. No. 8,754,865, entitled "MEDICAL MEASURING SYSTEM AND METHOD" and issued on Jun. 17, 2014, and U.S. Patent Application No. 61/473,570, entitled "MULTI-MODALITY MEDICAL SENSING SYSTEM AND METHOD" and filed on Apr. 8, 2011, both of which are hereby incorporated by reference herein in their entireties.

In the medical sensing system 100, the PIM 112 and PIM 114 are operable to respectively receive medical sensing data collected from the patient 106 by the medical sensing device 108 and medical sensing device 110 and are operable to transmit the received data to the processing system 124. In one embodiment, the PIM 112 and PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. Additionally, the ECG device 116 is operable to transmit electrocardiogram signals or other hemodynamic data from patient 106 to the processing system 124. To aid the clinician in data capture, the bedside interface 102 is operable to display the ECG data alongside medical sensing data. Further, in some embodiments, the processing system 124 may be operable to synchronize data collection with the catheters 108 and 110 using ECG signals from the ECG 116. Further, the angiogram system 117 is operable to collect x-ray, computed tomography (CT), or magnetic resonance images (MRI) of the patient 106 and transmit them to the processing system 124. After the x-ray, CT, or MRI data has been processed into human-readable images by the processing system 124, the clinician 107 may navigate the GUI on the bedside interface 124 to retrieve the images from the processing system 124 and display them on the interface. In some embodiments, the processing system 124 may co-register image data from angiogram system 117 (e.g. x-ray data, MM data, CT data, etc.) with sensing data from the catheters 108 and 110. As one aspect of this disclosure, the co-registration may be performed to generate three-dimensional images with the sensing data. Such co-registered 3-D images data may be viewable on the bedside interface 124. In one embodiment, a clinician may rotate, zoom, and otherwise manipulate such 3-D images on the bedside interface 102 using simultaneous touch inputs (i.e. multitouch) and gestures.

Additionally, in the illustrated embodiment of FIG. 1, medical sensing tools in system 100 are communicatively coupled to the processing system 124 via a wired connection such as a standard copper link or a fiber optic link. Specifically, the bedside interface 124 may be communicatively and/or electrically coupled to the processing system 124 via a Universal Serial Bus (USB) connection, a Power-over-Ethernet connection, a Thunderbolt connection, a FireWire connection, or some other high-speed data bus connection.

Figure 2:
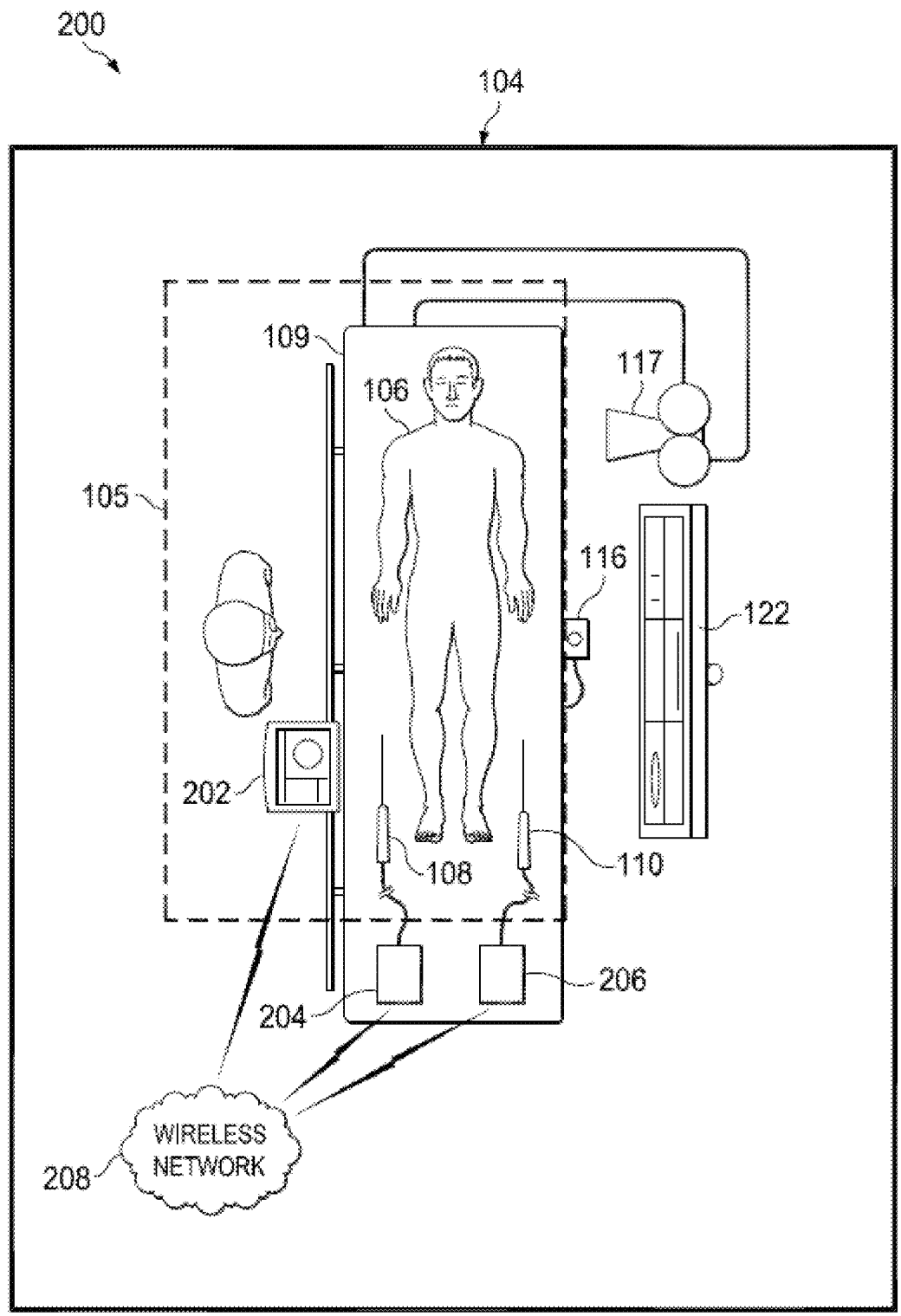
FIG. 2 is a schematic drawing depicting a medical sensing system including a wireless bedside interface according to another embodiment of the present disclosure.

However, in an alternative embodiment, such as that shown in FIG. 2, the medical sensing tools may communicate wirelessly. In that regard, FIG. 2 is a schematic drawing depicting a medical sensing system 200 including a wireless bedside interface 202 according to another embodiment of the present disclosure. The medical sensing system 200 is similar to the system 100 of FIG. 1 but the medical sensing tools including the wireless bedside interface 202, a wireless PIM 204, and a wireless PIM 206 communicate with a wireless network 208 via wireless networking protocols. For example, the bedside interface 202 may send and receive workflow control parameters, medical sensing images, and measurement data to and from a remote processing system via IEEE 802.11 Wi-Fi standards, Ultra Wide-Band (UWB) standards, wireless FireWire, wireless USB, Bluetooth, or another high-speed wireless networking standard. Such wireless capability allows the clinician 107 to more freely position the bedside interface 202 inside or outside of the sterile field 105 for better workflow management.

Figure 3:
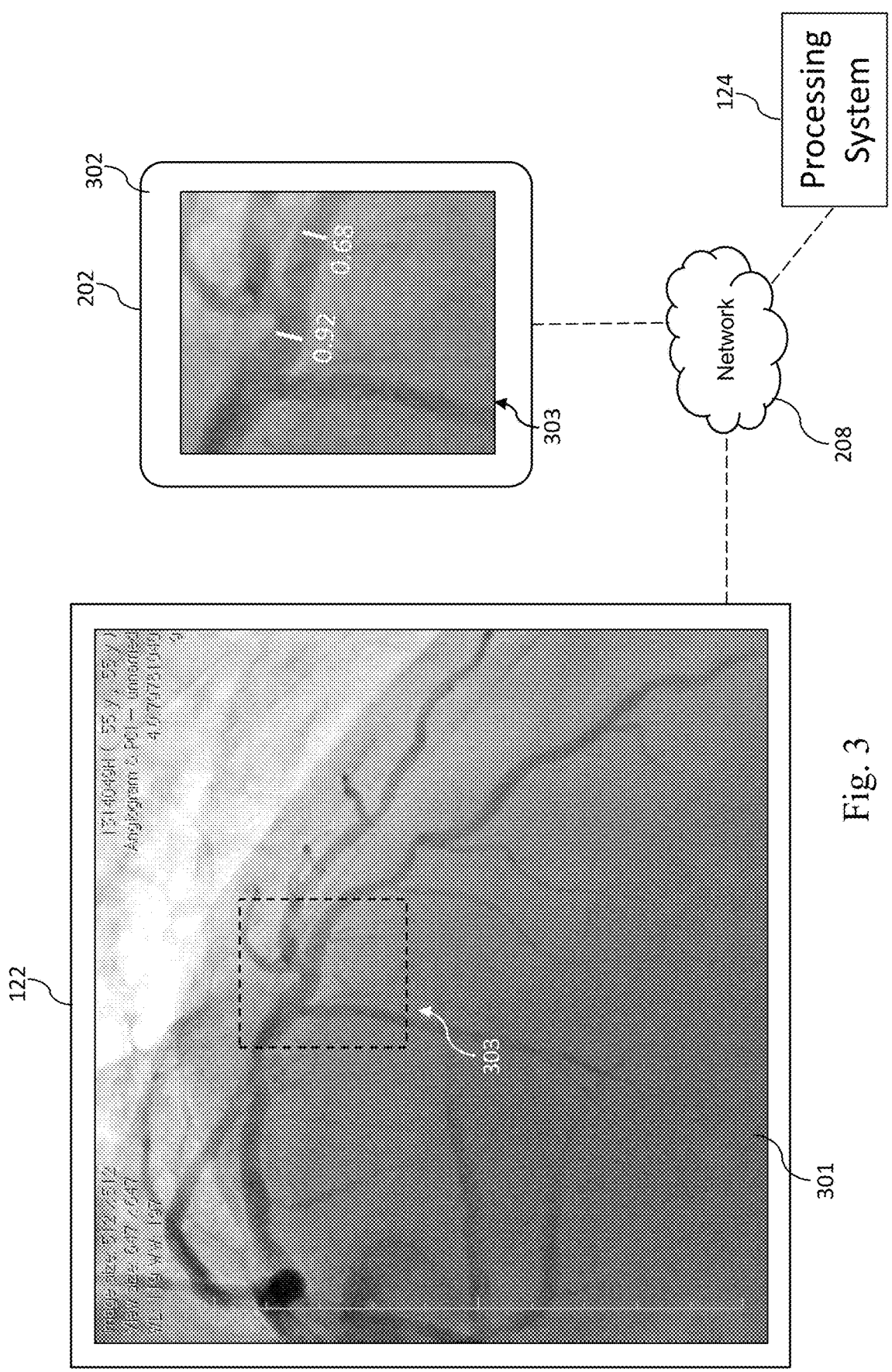
FIG. 3 is a schematic drawing depicting medical imagery displays on the boom display and bedside interface according to one embodiment of the present disclosure.

With reference now to FIG. 3, the bedside interface 202 includes an integrally formed housing 302 that is easy to grasp and move around a catheter lab or other medical setting. In one embodiment, the integrally formed housing 302 may be seamlessly molded from materials such as thermoplastic or thermosetting plastic or moldable metal. In other embodiments, the integrally formed housing 302 may comprise a plurality of housing portions fixedly bonded in a substantially permanent manner to form an integral housing. The housing 302 is resistant to fluids, and, in one embodiment, may have a rating of IPX4 against fluid ingress as defined by the International Electrotechnical Commission (IEC) standard 60529. In other embodiments in which the housing 302 may be used in different environments, the hub may have a different fluid ingress rating. In the illustrated embodiment, the housing 302 has a width, height, or thickness that is conducive to portability.

Still referring to the example of FIG. 3, the bedside interface 202 is configured to be used in conjunction with the boom display 122. In one embodiment, the bedside interface 202 and boom display 122 receive data obtained by intravascular sensors and/or imaging components and display corresponding medical imagery 301. Such imagery 301 can include static images, video, 3-D renderings, raw sensor or imaging data, filtered sensor or imaging data, calculated sensor or imaging data, and/or other data representative of the patient's anatomy. This data may be collected during a diagnostic procedure or may be collected during a surgical procedure, such as PCI. In one embodiment, diagnostic visualizations are overlaid on images of a vessel displayed on the boom display 122 and/or bedside interface 202. These diagnostic visualizations may assist the clinician 107 in determining the best available treatment options for a particular patient.

The diagnostic visualizations can include markings, colors, numerical values, or other representations of the data obtained from medical instruments, such as guidewires and catheters. In that regard, the diagnostic visualizations can include intensity maps based on recorded pressure measurements and may incorporate graphs of corresponding pressure ratios. Further, the diagnostic visualizations may be overlaid onto extravascular images such as two-dimensional angiographic images, three-dimensional angiographic images, and computed tomography angiographic (CTA) images, and intravascular images such as ultrasound (IVUS) images and optical coherence tomography (OCT) images. In some instances, the diagnostic visualizations can include one type of image overlaid onto another type of image. Further, one or more treatment options can be simulated and the diagnostic visualizations updated based on the parameters associated with each particular simulated treatment option. In this manner, an estimated result or outcome for each treatment option can be visually provided to the clinician. The diagnostic visualizations and/or simulated treatments can be carried out as described in one or more of PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/895,909, filed Oct. 25, 2013 and titled "Devices, Systems, and Methods for Vessel Assessment," U.S. Provisional Patent Application No. 61/943,168, filed Feb. 21, 2014 and titled "DEVICES, SYSTEMS, AND METHODS AND ASSOCIATED DISPLAY SCREENS FOR ASSESSMENT OF VESSELS," U.S. Provisional Patent Application No. 62/024,005, filed Jul. 14, 2014 and titled "DEVICES, SYSTEMS, AND METHODS FOR TREATMENT OF VESSELS," each of which is hereby incorporated by reference in its entirety.

Based on the image(s), diagnostic visualization(s), and/or simulated treatments, a clinician can determine the best treatment option for the patient. Medical supervisors may also use the bedside interface 202 to check the work of clinicians 107 or to offer second opinions to a patient 106. Diagnostic visualizations may also be presented to a patient 106 or a caretaker of a patient 106 to assist a clinician 107 in explaining testing results or treatment options. Additionally, the bedside interface 202 may be used to guide the placement of treatment devices during a procedure. In this case, a clinician 107 may use the bedside interface 202 to check the location of medical instruments, guidewires, or stents to ensure positional accuracy during the procedure.

A portion 303 of the imagery 301 is displayed on the bedside interface 202 to allow a clinician 107 to view specific areas of interest in the imagery 301. The bedside interface 202 is equipped with a touch screen interface, allowing a clinician 107 to easily manipulate imagery 301 using simultaneous touch inputs and gestures. The bedside interface 202 is configured to be able to zoom into areas of interest and display images, graphical information, and text relating to the imagery 301. FIG. 3 shows that zoomed in portion 303 of the general imagery 301 that is displayed on the bedside interface 202. In the illustrated embodiment, a communication network 208 connects the boom display 122 and the bedside interface 202 to the processing system 124. A wireless connection to the bedside interface 202 may be favored during diagnostic procedures to allow a clinician 107 to carry, reposition, or move the bedside display 202 as desired. This allows for continual monitoring of certain key aspects of the procedure, and may allow a clinician 107 to communicate diagnostic information and treatment options with a patient 106, another clinician 107, and/or a caretaker or family member of the patient.

As shown in FIG. 3, the bedside display 202 may also be used to display additional or more detailed diagnostic information for the portion 303 corresponding to the region of interest of the vessel. In this example, the boom display 122 displays imagery 301 of a patient while the bedside interface 202 shows the portion 303 of interest with diagnostic visualizations overlaid. In the example shown in FIG. 3, pressure ratios, such as FFR or iFR values, are shown along the region of interest of the vessel. As shown, there is a significant drop in the pressure ratio from 0.92 to 0.68 that can be indicative of a severe blockage or lesion. It is understood that any of a number of other types of diagnostic visualizations may be utilized as described above.

Figure 4:
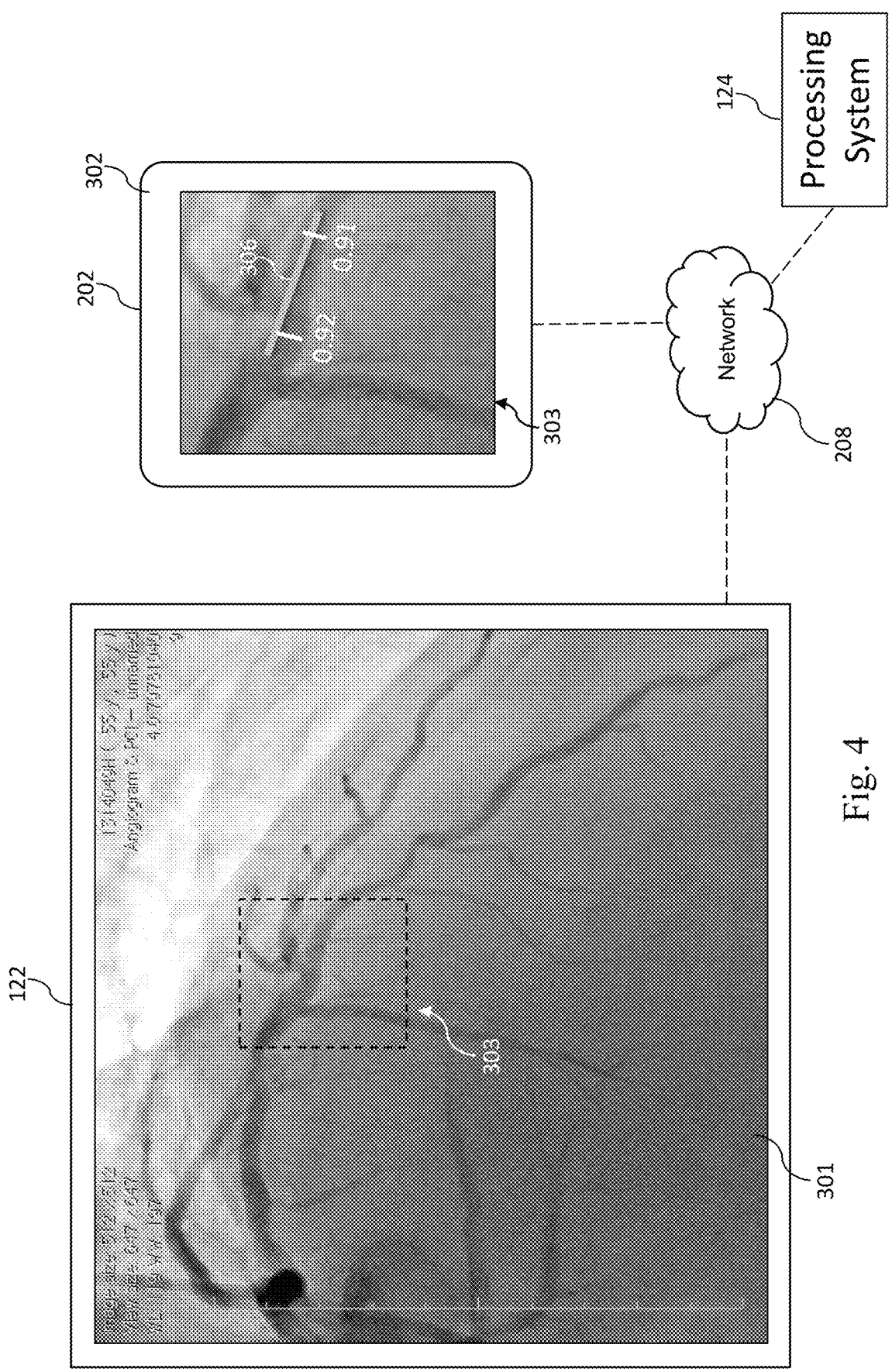
FIG. 4 is a schematic drawing depicting medical imagery displays on the boom display and bedside interface according to one embodiment of the present disclosure.

Further, one or more treatment options can be simulated and the diagnostic visualizations displayed on the bedside display 202 can be updated based on the parameters associated with a particular simulated treatment option. FIG. 4 shows an example of this approach. In particular, FIG. 4 shows the simulated deployment of a stent 306 and the corresponding resulting change in the diagnostic visualizations. In particular, the severe drop to 0.68 shown FIG. 3 is estimated to be improved significantly by deployment of the stent to a value of 0.91. Using this or similar approaches with other diagnostic visualization information, estimated results or outcomes for each treatment option can be visually provided to the clinician on the bedside display 202 and/or the overhead boom display 122. A simulated procedure may be displayed on the bedside interface 202 to show the likely outcome of a procedure. A simulated stent 306 is shown on the bedside interface 202 as well as statistical data 303 on the size and position of the stent. A clinician 107 may also place markers 305 on the imagery 301 of the bedside interface 202 to indicate important areas or provide ongoing pressure measurements. Simulations such as those shown in FIG. 4 may afford a clinician 107 a view of both the predicted result of a procedure on the beside interface 202 and real-time imagery 301 of the patient on the boom display 122, affording a detailed and readily understandable analysis of treatment options. This analysis is also easily shared with a patient 106 or a patient's guardian or caretaker.

Figure 5:
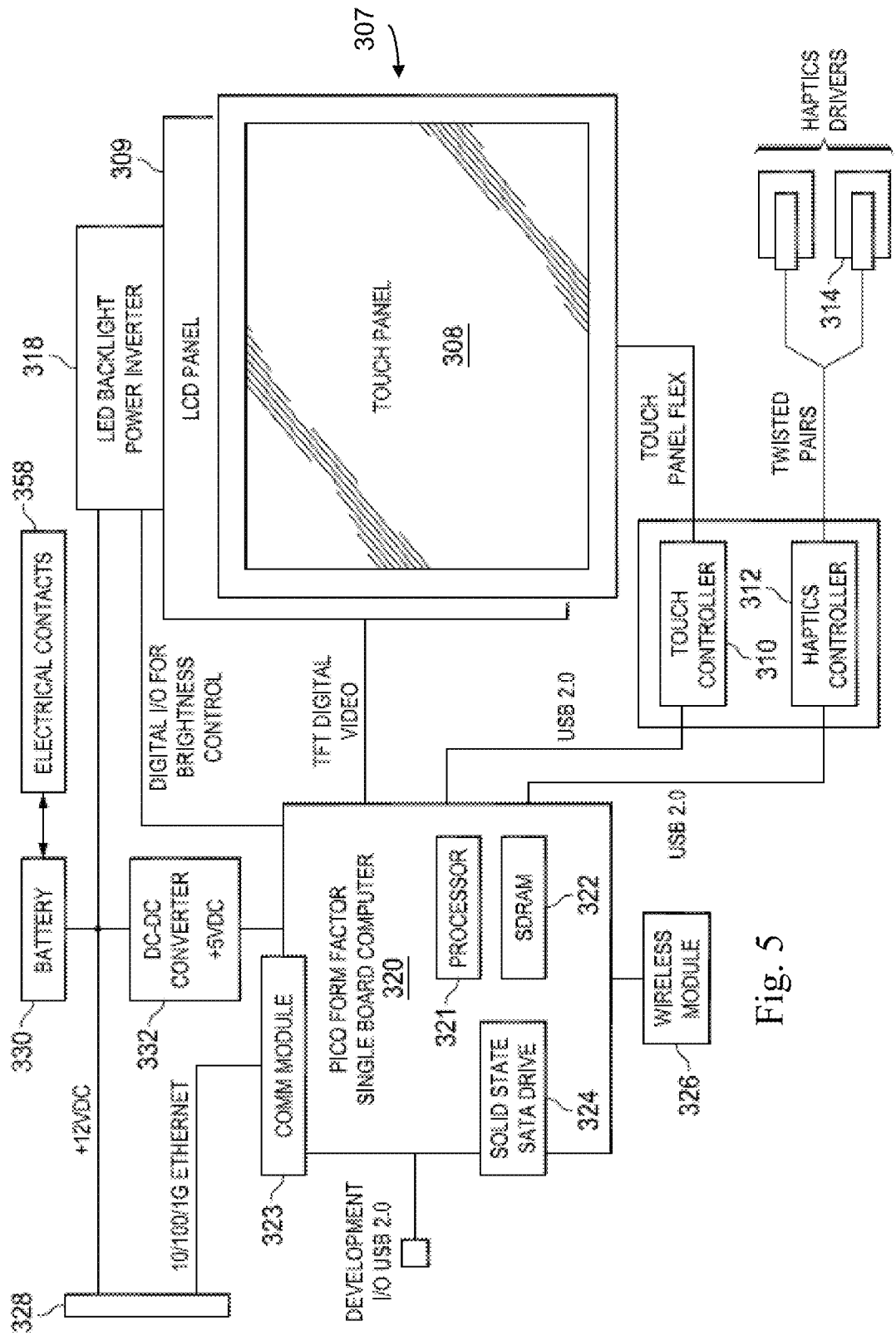
FIG. 5 is a functional block diagram of the bedside interface of FIGS. 3A-3C according to aspects of the present disclosure.

FIG. 5 shows a functional block diagram of the bedside controller 300 according to aspects of the present disclosure. Embedded into the front of the housing 302 is the touch-sensitive display 307 that comprises both a touch panel 308 and a flat panel display 309. The touch panel 308 overlays the flat panel display 308 and accepts user input via human touch, stylus touch, or some other analogous input method. In other words, the touch-sensitive display 307 displays images and accepts user input on the same surface. In the current embodiment, the touch panel 308 is a resistive-type panel, but in alternative embodiments it may be a capacitive-type panel, projective-type panel, or some other suitable type of touch enabled input panel. Further, the touch panel 308 is operable to accept multiple inputs simultaneously (multitouch), for instance, to enable rotation of a three-dimensional rendering of a vessel along multiple axes. Additionally, the touch panel 308 is capable of receiving input when a sterile drape 301 is covering the bedside interface 300 and also when a user is gloved. The touch panel 308 is controlled by a touch interface 310 disposed within the housing 302. Further, when a clinician makes contact with the touch panel 308, the touch panel is operable to provide haptic feedback via a haptics interface 312 and haptics drivers 314. This haptic technology is operable to simulate a plurality of sensations on the touch panel 308 by varying the intensity and frequency of vibrations generated when a user contacts the touch panel. In some embodiments, the housing 302 may include a sheath configured to store a stylus therein. Thus, a clinician may remove the stylus from the sheath in the housing to make measurements on the bedside interface and store it when the measurements have been completed.

Beneath the touch panel 308 is the flat panel display 309 that presents a graphical user interface (GUI) 316 to a user. In the illustrated embodiment, the flat panel display 309 is a LCD display but in alternative embodiments, it may be a different type of display such an LED display or an AMO-LED display. In the illustrated embodiment, the flat panel display 309 is illuminated by a LED backlight power inverter 318. As mentioned above, the GUI 316 not only allows a clinician to control a medical sensing workflow, but also view and interact with pressure data obtained from a patient in the sterile field.

The bedside interface 300 includes a single board processing platform 320 within the housing 302 that is operable to render the GUI 316 and process user touch input. In the illustrated embodiment, the processing platform has a pico form factor and includes integrated processing components such as a processor 321, system memory 322, graphics processing unit (GPU), communications module 323, and I/O bus interface. In some embodiments, the processor 321 may be a low power processor such as an Intel Atom® processor or an ARM-based processor, and the communications module 323 may be a 10/100/1 Gb Ethernet module. And, the I/O bus interface may be a Universal Serial Bus (USB) interface. The bedside interface 300 further includes a storage module 324 that is a non-transitory computer readable storage medium operable to store an operating system (i.e. software to render and control the GUI), data and/or visual representation manipulation software, medical sensing data and visual representations received from a processing system, and other medical sensing-related software. The processor 321 is configured to execute software and instructions stored on the storage module 324. In the illustrated embodiment, the storage module 324 is a solid state drive (SSD) hard drive communicatively coupled to the processing platform 320 via a SATA connection, but, in alternative embodiments, it may be any other type of non-volatile or temporary storage module. The bedside interface 300 further includes a wireless communications module 326 communicatively coupled to the processing platform 320. In some embodiments, the wireless communications module is a IEEE 802.11 Wi-Fi module, but in other may be an Ultra Wide-Band (UWB) wireless module, a wireless FireWire module, a wireless USB module, a Bluetooth module, or another high-speed wireless networking module.

In the illustrated embodiment, the bedside interface 300 is powered via both a wired 12 VDC power-over-Ethernet (PoE) connection 328 and a battery 330 disposed within the housing 302. In one embodiment, the battery 330 may be sealed within the integrally formed housing 302 and may be recharged through electrical contacts disposed on the exterior of the housing and electrically coupled to the battery. As shown in the embodiment of FIG. 3B, the front wall 350 may include one or more electrical contacts 358 through which the battery 330 may be charged when the interface is mounted to objects with compatible charging structure. In other embodiments, the housing 302 may include a battery compartment with a removable cover to permit battery replacement. Such a battery compartment cover may be resistant to fluid ingress (e.g., with an IPX4 rating). The beside interface 300 may be coupled to a processing system in the catheter lab via the PoE connection 328, over which it receives medical sensing images that have been captured from the patient and rendered on the processing system. In operation, when the bedside interface is coupled to the PoE connection 328, it receives power and communications over the same physical wire. When the bedside interface 300 is disconnected from the PoE connection 328, it runs on battery power and receives data wirelessly via the wireless communications module 326. When used wirelessly in a catheter lab, the beside interface may directly communicate with a processing system (i.e. in an ad-hoc wireless mode), or, alternatively, it may communicate with a wireless network that serves a plurality of wireless devices. In alternative embodiments, the bedside interface 300 may receive power and data through different wired connections, or receive data communications through a wired data connection and power from the battery 330, or receive data communications through the wireless module 326 and power from a wired electrical connection. In some embodiments, the bedside interface 300 may be used in a semi-wireless configuration, in which the battery 330 provides backup power to the interface when the interface is temporarily disconnected from a wired power source. For example, if at the beginning of a procedure, the bedside interface 300 is connected to a PoE connection (or other type of wired connection) and during the procedure the interface must be disconnected from the PoE connection to allow for a cabling adjustment, the battery 330 may keep the interface alive until a PoE connection can be re-established. In this manner, a full power-off and reboot of the interface 300 is avoided during a procedure. As shown in FIG. 4, a DC-DC power converter 332 converts input voltage to a voltage usable by the processing platform 320.

It is understood that although the bedside interface 300 includes specific components described herein, the bedside interface may include any number of additional components, for example a charge regulator interposed between the electrical contacts and the battery, and may be configured in any number of alternative arrangements in alternative embodiments.

Figure 6:
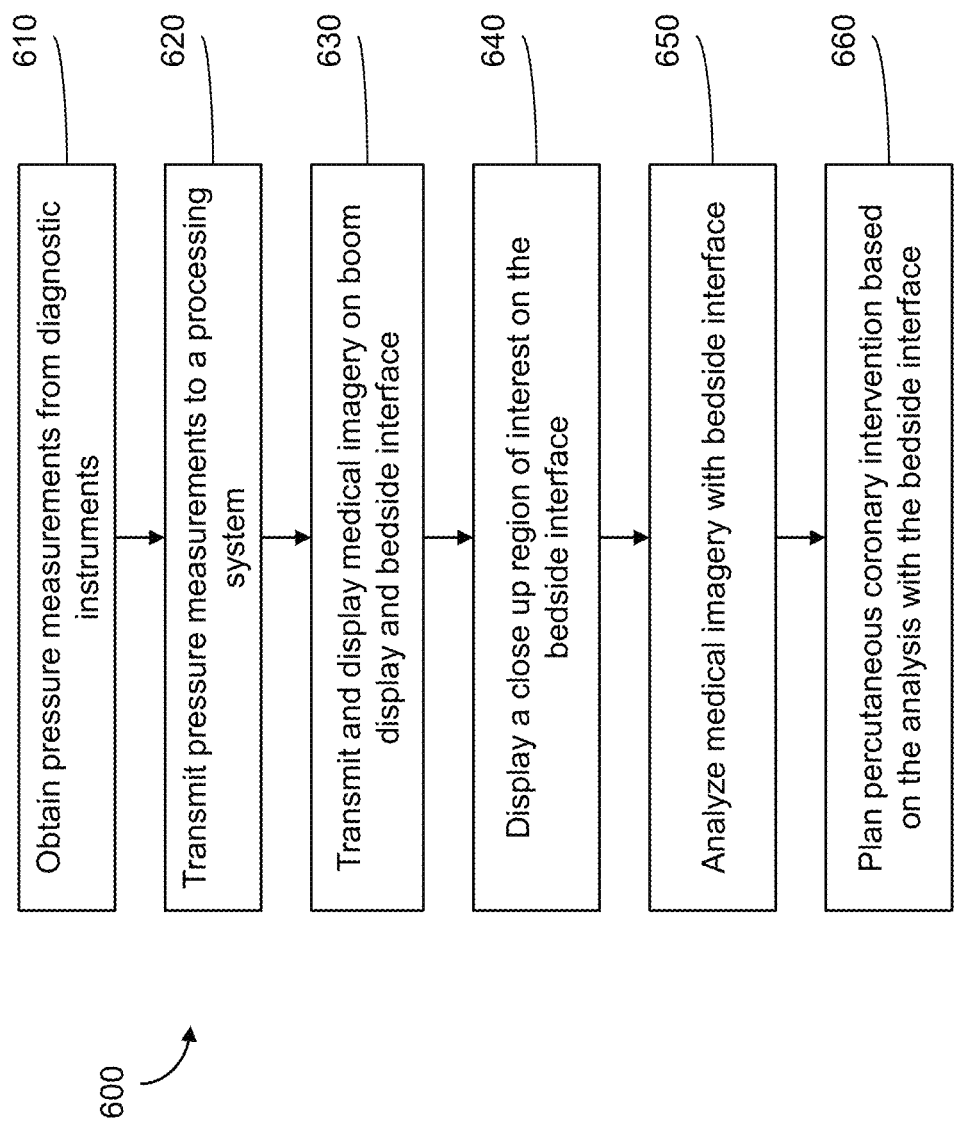
FIG. 6 is a flowchart illustrating a method of conducting a medical sensing workflow with a bedside interface according to various aspects of the present disclosure.

FIG. 6 is a flowchart illustrating a method 600 of planning the treatment of a patient. The method 600 will be described in the context of a pressure-sensing procedure, such as an iFR procedure, but may equally apply to any number of medical sensing or treatment procedures, such as an FFR procedure, an IVUS procedure, OCT procedure, a FLIVUS procedure, an ICE procedure, etc. The method 600 can be better understood with reference to the FIGS. 7-10.

Figure 7:
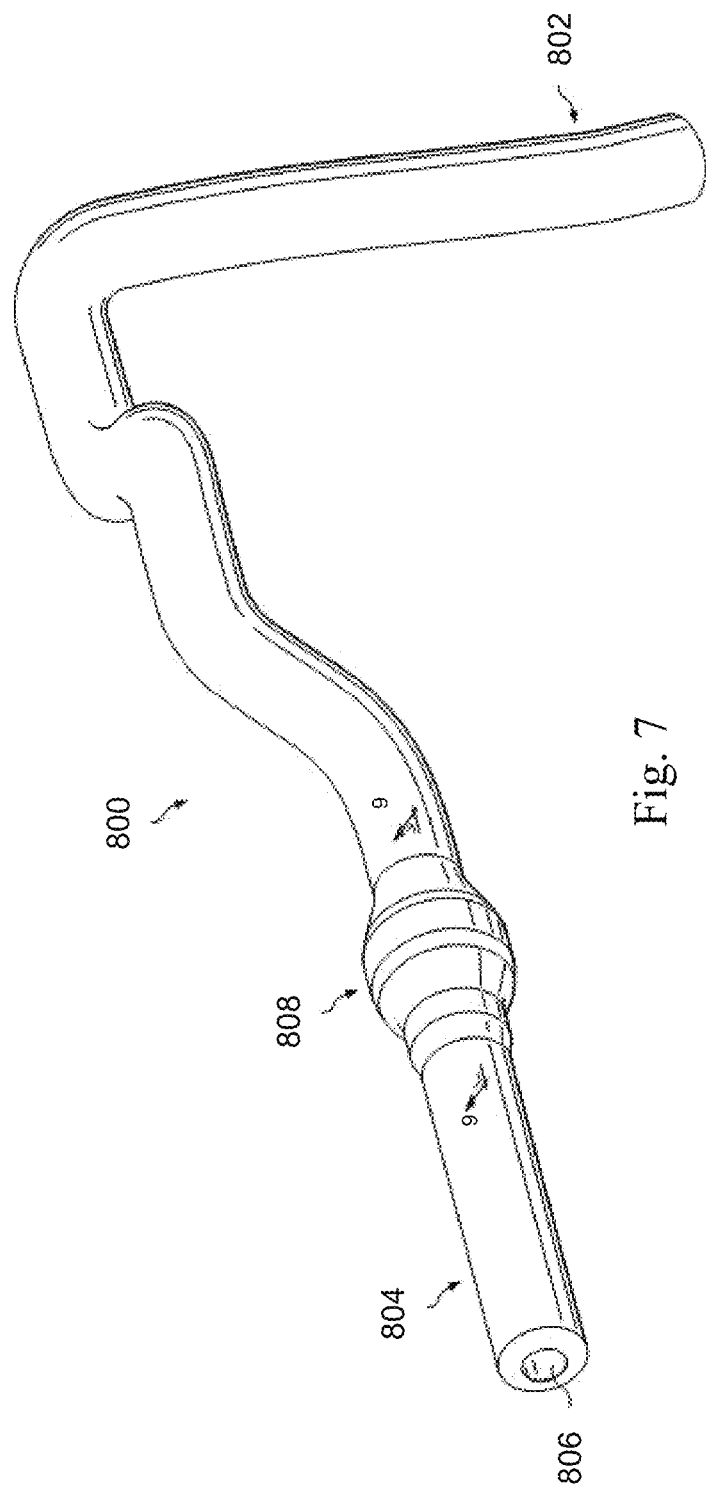
FIG. 7 shows a diagrammatic perspective view of a vessel having a stenosis according to an embodiment of the present disclosure.
Figure 8:
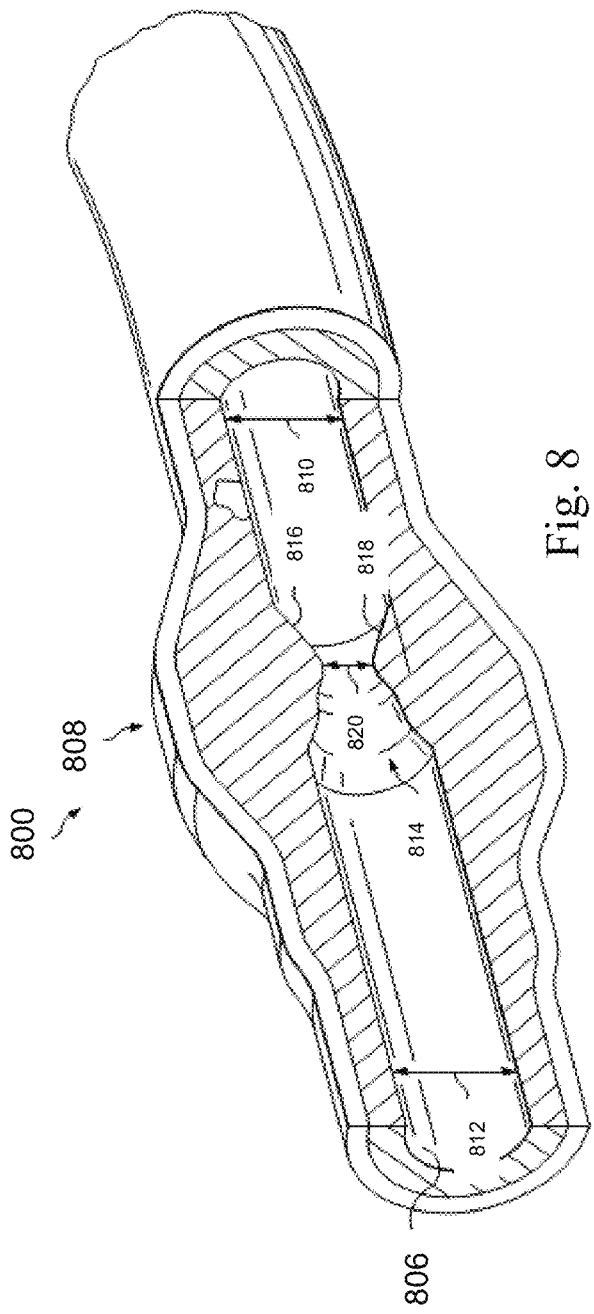
FIG. 8 shows a diagrammatic, partial cross-sectional perspective view of a portion of the vessel of FIG. 7 taken along section line 9-9 of FIG. 7.

In that regard, referring to FIGS. 7 and 8, shown therein is a vessel 800 having a stenosis according to an embodiment of the present disclosure. In that regard, FIG. 7 is a diagrammatic perspective view of the vessel 800, while FIG. 8 is a partial cross-sectional perspective view of a portion of the vessel 800. Referring more specifically to FIG. 7, the vessel 800 includes a proximal portion 802 and a distal portion 804. A lumen 806 extends along the length of the vessel 800 between the proximal portion 802 and the distal portion 804. In that regard, the lumen 806 is configured to allow the flow of fluid through the vessel. In some instances, the vessel 800 is a blood vessel. In some particular instances, the vessel 800 is a coronary artery. In such instances, the lumen 806 is configured to facilitate the flow of blood through the vessel 800.

As shown, the vessel 800 includes a stenosis 808 between the proximal portion 802 and the distal portion 804. Stenosis 808 is generally representative of any blockage or other structural arrangement that results in a restriction to the flow of fluid through the lumen 806 of the vessel 800. Embodiments of the present disclosure are suitable for use in a wide variety of vascular applications, including without limitation coronary, peripheral (including but not limited to lower limb, carotid, and neurovascular), renal, and/or venous. Where the vessel 800 is a blood vessel, the stenosis 808 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 8, the lumen 806 of the vessel 800 has a diameter 810 proximal of the stenosis 808 and a diameter 812 distal of the stenosis. In some instances, the diameters 810 and 812 are substantially equal to one another. In that regard, the diameters 810 and 812 are intended to represent healthy portions, or at least healthier portions, of the lumen 806 in comparison to stenosis 808. Accordingly, these healthier portions of the lumen 806 are illustrated as having a substantially constant cylindrical profile and, as a result, the height or width of the lumen has been referred to as a diameter. However, it is understood that in many instances these portions of the lumen 806 will also have plaque buildup, a non-symmetric profile, and/or other irregularities, but to a lesser extent than stenosis 808 and, therefore, will not have a cylindrical profile. In such instances, the diameters 810 and 812 are understood to be representative of a relative size or cross-sectional area of the lumen and do not imply a circular cross-sectional profile.

As shown in FIG. 8, stenosis 808 includes plaque buildup 814 that narrows the lumen 806 of the vessel 800. In some instances, the plaque buildup 814 does not have a uniform or symmetrical profile, making angiographic evaluation of such a stenosis unreliable. In the illustrated embodiment, the plaque buildup 814 includes an upper portion 816 and an opposing lower portion 818. In that regard, the lower portion 818 has an increased thickness relative to the upper portion 816 that results in a non-symmetrical and non-uniform profile relative to the portions of the lumen proximal and distal of the stenosis 808. As shown, the plaque buildup 814 decreases the available space for fluid to flow through the lumen 806. In particular, the cross-sectional area of the lumen 806 is decreased by the plaque buildup 814. At the narrowest point between the upper and lower portions 816, 818 the lumen 806 has a height 820, which is representative of a reduced size or cross-sectional area relative to the diameters 810 and 812 proximal and distal of the stenosis 808. Note that the stenosis 808, including plaque buildup 814 is exemplary in nature and should be considered limiting in any way. In that regard, it is understood that the stenosis 808 has other shapes and/or compositions that limit the flow of fluid through the lumen 806 in other instances. While the vessel 800 is illustrated in FIGS. 7 and 8 as having a single stenosis 808 and the description of the embodiments below is primarily made in the context of a single stenosis, it is nevertheless understood that the devices, systems, and methods described herein have similar application for a vessel having multiple stenosis regions.

Figure 9:
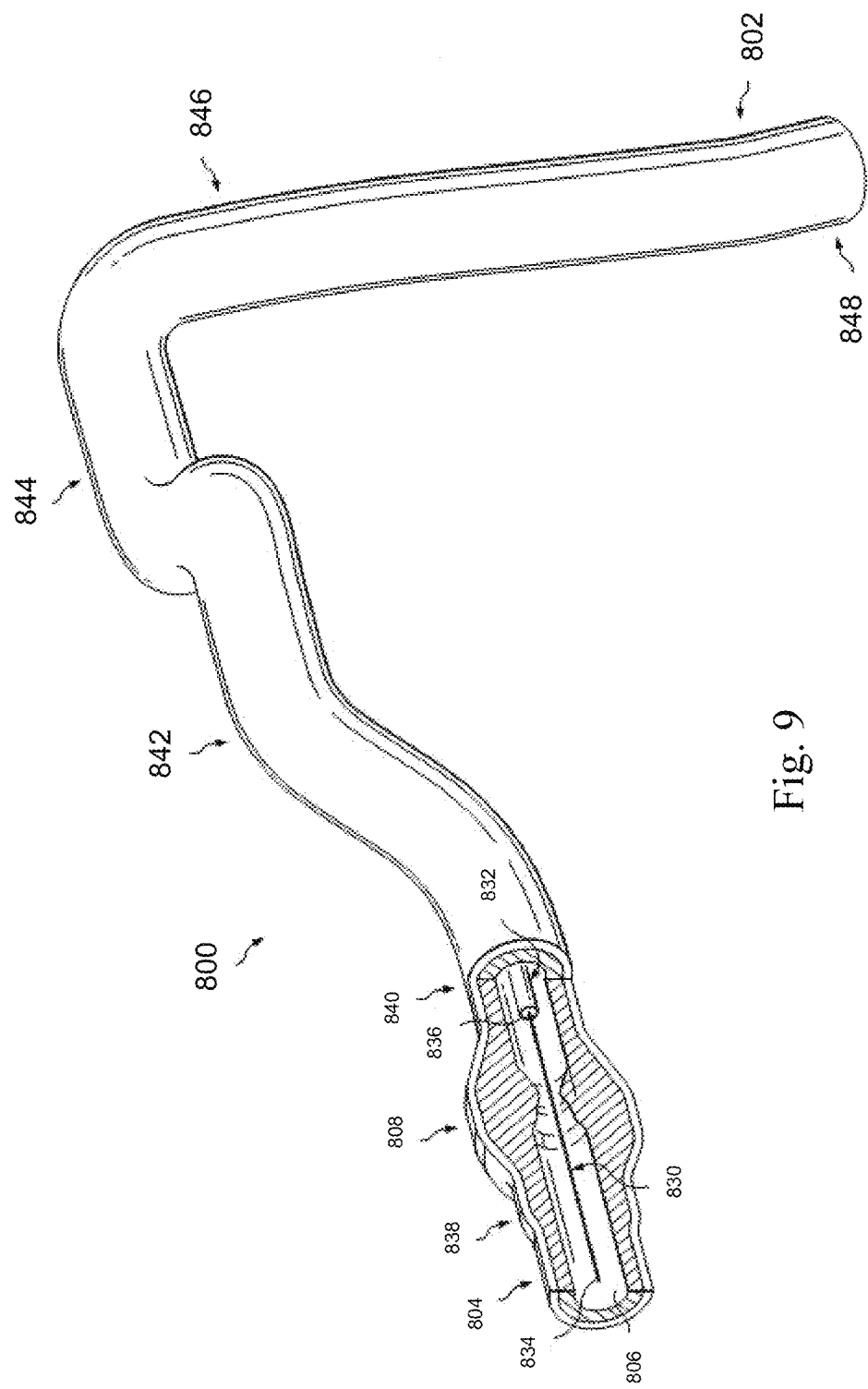
FIG. 9 shows a diagrammatic, partial cross-sectional perspective view of the vessel of FIGS. 7 and 8 with instruments positioned therein according to an embodiment of the present disclosure.

Referring now to FIG. 9, the vessel 800 is shown with instruments 830 and 832 positioned therein according to an embodiment of the present disclosure. In general, instruments 830 and 832 may be any form of device, instrument, or probe sized and shaped to be positioned within a vessel. The instruments 830 and 832 can be implemented in the medical sensing system 100 (FIG. 1) as medical sensing devices 108 and 110. In the illustrated embodiment, instrument 830 is generally representative of a guide wire, while instrument 832 is generally representative of a catheter. In that regard, instrument 830 extends through a central lumen of instrument 832. However, in other embodiments, the instruments 830 and 832 take other forms. In that regard, the instruments 830 and 832 are of similar form in some embodiments. For example, in some instances, both instruments 830 and 832 are guide wires. In other instances, both instruments 830 and 832 are catheters. On the other hand, the instruments 830 and 832 are of different form in some embodiments, such as the illustrated embodiment, where one of the instruments is a catheter and the other is a guide wire. Further, in some instances, the instruments 830 and 832 are disposed coaxial with one another, as shown in the illustrated embodiment of FIG. 9. In other instances, one of the instruments extends through an off-center lumen of the other instrument. In yet other instances, the instruments 830 and 832 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 830 and 832 a single instrument is utilized. In some embodiments, the single instrument incorporates aspects of the functionalities (e.g., data acquisition) of both instruments 830 and 832.

Instrument 830 is configured to obtain diagnostic information about the vessel 800. In that regard, the instrument 830 includes one or more sensors, transducers, and/or other monitoring elements configured to obtain the diagnostic information about the vessel. The diagnostic information includes one or more of pressure, flow (velocity and/or volume), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 830 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 834 of the instrument 830 in some instances. In some instances, at least one of the one or more sensors, transducers, and/or other monitoring elements is positioned at the distal tip of the instrument 830.

The instrument 830 includes at least one element configured to monitor pressure within the vessel 800. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 830 is sized such that it can be positioned through the stenosis 808 without significantly impacting fluid flow across the stenosis, which would impact the distal pressure reading. Accordingly, in some instances the instrument 830 has an outer diameter of 0.018" or less. In some embodiments, the instrument 830 has an outer diameter of 0.014" or less.

Instrument 832 is also configured to obtain diagnostic information about the vessel 100. In some instances, instrument 832 is configured to obtain the same diagnostic information as instrument 830. In other instances, instrument 832 is configured to obtain different diagnostic information than instrument 830, which may include additional diagnostic information, less diagnostic information, and/or alternative diagnostic information. The diagnostic information obtained by instrument 832 includes one or more of pressure, flow (velocity and/or volume), images (including images obtained using ultrasound (e.g., IVUS), OCT, thermal, and/or other imaging techniques), temperature, and/or combinations thereof. Instrument 832 includes one or more sensors, transducers, and/or other monitoring elements configured to obtain this diagnostic information. In that regard, the one or more sensors, transducers, and/or other monitoring elements are positioned adjacent a distal portion of the instrument 832 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 836 of the instrument 832 in some instances. In some instances, at least one of the one or more sensors, transducers, and/or other monitoring elements is positioned at the distal tip of the instrument 832.

Similar to instrument 830, instrument 832 also includes at least one element configured to monitor pressure within the vessel 800. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 832 in some instances.

In accordance with aspects of the present disclosure, at least one of the instruments 830 and 832 is configured to monitor a pressure within the vessel 800 distal of the stenosis 808 and at least one of the instruments 830 and 832 is configured to monitor a pressure within the vessel proximal of the stenosis. In that regard, the instruments 830, 832 are sized and shaped to allow positioning of the at least one element configured to monitor pressure within the vessel 800 to be positioned proximal and/or distal of the stenosis 808 as necessary based on the configuration of the devices. In that regard, FIG. 9 illustrates a position 838 suitable for measuring pressure distal of the stenosis 808. In that regard, the position 838 is less than 5 cm, less than 3 cm, less than 2 cm, less than 1 cm, less than 5 mm, and/or less than 2.5 mm from the distal end of the stenosis 808 (as shown in FIG. 8) in some instances. FIG. 9 also illustrates a plurality of suitable positions for measuring pressure proximal of the stenosis 808. In that regard, positions 840, 842, 844, 846, and 848 each represent a position that is suitable for monitoring the pressure proximal of the stenosis in some instances. In that regard, the positions 840, 842, 844, 846, and 848 are positioned at varying distances from the proximal end of the stenosis 808 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 830 and 832 is configured to monitor pressure within the vessel 800 while being moved through the lumen 806. In some instances, instrument 830 is configured to be moved through the lumen 806 and across the stenosis 808. In that regard, the instrument 830 is positioned distal of the stenosis 808 and moved proximally (i.e., pulled back) across the stenosis to a position proximal of the stenosis in some instances. In other instances, the instrument 830 is positioned proximal of the stenosis 808 and moved distally across the stenosis to a position distal of the stenosis. Movement of the instrument 830, either proximally or distally, is controlled manually by medical personnel (e.g., hand of a surgeon) in some embodiments. In other embodiments, movement of the instrument 830, either proximally or distally, is controlled automatically by a movement control device (e.g., a pullback device, such as the Trak Back® II Device available from Volcano Corporation). In that regard, the movement control device controls the movement of the instrument 830 at a selectable and known speed (e.g., 2.0 mm/s, 1.0 mm/s, 0.5 mm/s, 0.2 mm/s, etc.) in some instances. Movement of the instrument 830 through the vessel is continuous for each pullback or push through, in some instances. In other instances, the instrument 830 is moved step-wise through the vessel (i.e., repeatedly moved a fixed amount of distance and/or a fixed amount of time). Some aspects of the visual depictions discussed below are particularly suited for embodiments where at least one of the instruments 830 and 832 is moved through the lumen 806. Further, in some particular instances, aspects of the visual depictions discussed below are particularly suited for embodiments where a single instrument is moved through the lumen 806, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guide wire relative to the pressure reading of a guide catheter. In that regard, because FFR is calculated as the ratio of the pressure measurement obtained by the guide wire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 10:
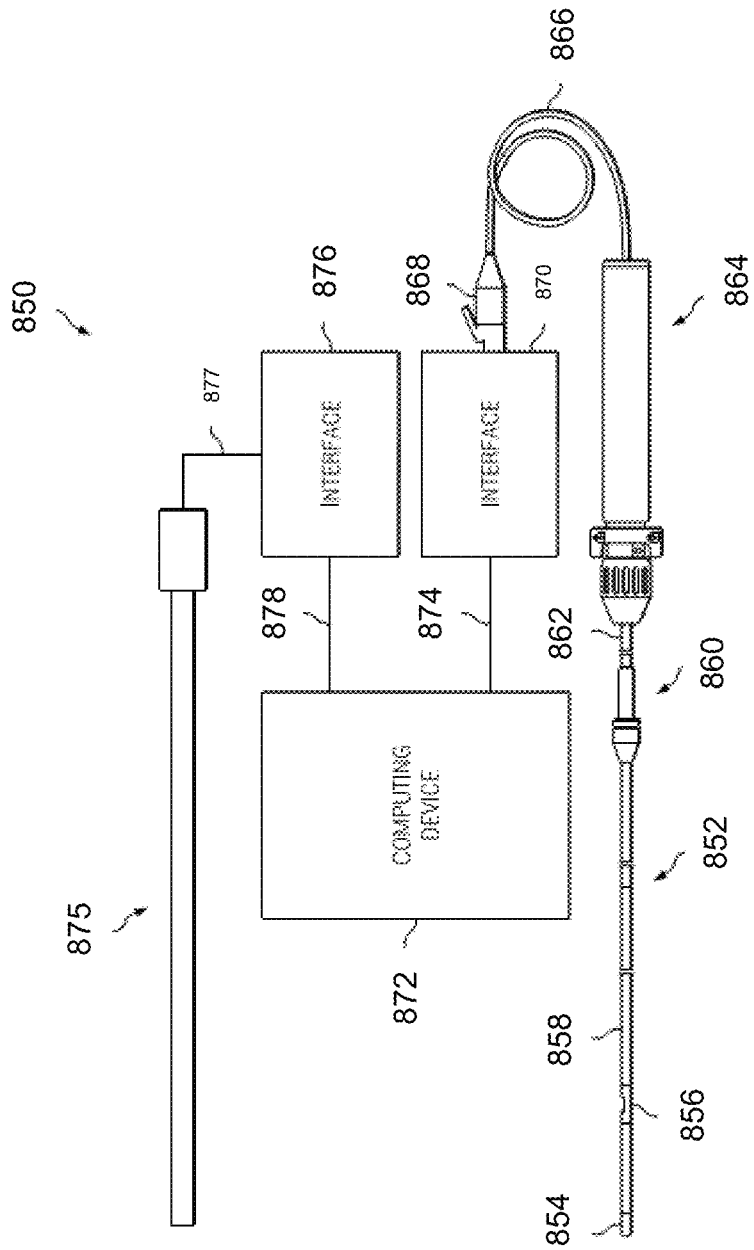
FIG. 10 shows a diagrammatic, schematic view of a system according to an embodiment of the present disclosure.

Referring now to FIG. 10, shown therein is a system 850 according to an embodiment of the present disclosure. In that regard, FIG. 10 is a diagrammatic, schematic view of the system 850. In some embodiments, the system 850 can be implemented as the medical sensing system 100 (FIG. 1). In some embodiments, one or more components of the medical sensing system 100 can be additionally implemented in the system 850, such as a bedside interface having a touch-sensitive display. As shown, the system 850 includes an instrument 852. In that regard, in some instances instrument 852 is suitable for use as at least one of instruments 830 and 832 (FIGS. 8-10) and/or medical sensing devices 108 and 110 (FIG. 1), discussed above. Accordingly, in some instances the instrument 852 includes features similar to those discussed above with respect to instruments 830 and 832 in some instances. In the illustrated embodiment, the instrument 852 is a guide wire having a distal portion 854 and a housing 856 positioned adjacent the distal portion. In that regard, the housing 856 is spaced approximately 3 cm from a distal tip of the instrument 852. The housing 856 is configured to house one or more sensors, transducers, and/or other monitoring elements configured to obtain the diagnostic information about the vessel. In the illustrated embodiment, the housing 856 contains at least a pressure sensor configured to monitor a pressure within a lumen in which the instrument 852 is positioned. A shaft 858 extends proximally from the housing 856. A torque device 860 is positioned over and coupled to a proximal portion of the shaft 858. A proximal end portion 862 of the instrument 852 is coupled to a connector 864. A cable 866 extends from connector 864 to a connector 868. In some instances, connector 868 is configured to be plugged into an interface 870. In that regard, interface 870 is a patient interface module (PIM) in some instances. The interface 870 can be implemented as the PIM 112 (FIG. 1). In some instances, the cable 866 is replaced with a wireless connection. In that regard, it is understood that various communication pathways between the instrument 852 and the interface 870 may be utilized, including physical connections (including electrical, optical, and/or fluid connections), wireless connections, and/or combinations thereof.

The interface 870 is communicatively coupled to a computing device 872 via a connection 874. Computing device 872 is generally representative of any device suitable for performing the processing and analysis techniques discussed within the present disclosure. In some embodiments, the computing device 872 includes a processor, random access memory, and a storage medium. In that regard, in some particular instances the computing device 872 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 872 is the bedside interface. For example, the processing steps described herein can be performed by one or more processing components of the bedside interface, such as the processing platform 320. In some instances, the computing device 872 is a console device. In some particular instances, the computing device 872 is similar to the s5™ Imaging System or the s5i™ Imaging System, each available from Volcano Corporation. In some instances, the computing device 872 is portable (e.g., handheld, on a rolling cart, etc.). Further, it is understood that in some instances the computing device 872 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 864, cable 866, connector 868, interface 870, and connection 874 facilitate communication between the one or more sensors, transducers, and/or other monitoring elements of the instrument 852 and the computing device 872. However, this communication pathway is exemplary in nature and should not be considered limiting in any way. In that regard, it is understood that any communication pathway between the instrument 852 and the computing device 872 may be utilized, including physical connections (including electrical, optical, and/or fluid connections), wireless connections, and/or combinations thereof. In that regard, it is understood that the connection 874 is wireless in some instances. In some instances, the connection 874 includes a communication link over a network (e.g., intranet, internet, telecommunications network, and/or other network). In that regard, it is understood that the computing device 872 is positioned remote from an operating area where the instrument 152 is being used in some instances. Having the connection 874 include a connection over a network can facilitate communication between the instrument 852 and the remote computing device 872 regardless of whether the computing device is in an adjacent room, an adjacent building, or in a different state/country. Further, it is understood that the communication pathway between the instrument 852 and the computing device 872 is a secure connection in some instances. Further still, it is understood that, in some instances, the data communicated over one or more portions of the communication pathway between the instrument 852 and the computing device 872 is encrypted.

The system 850 also includes an instrument 875. In that regard, in some instances instrument 875 is suitable for use as at least one of instruments 130 and 132 (FIGS. 7-9) and/or medical sensing devices 108 and 110 (FIG. 1), discussed above. Accordingly, in some instances the instrument 875 includes features similar to those discussed above with respect to instruments 130 and 132 in some instances. In the illustrated embodiment, the instrument 875 is a catheter-type device. In that regard, the instrument 875 includes one or more sensors, transducers, and/or other monitoring elements adjacent a distal portion of the instrument configured to obtain the diagnostic information about the vessel. In the illustrated embodiment, the instrument 875 includes a pressure sensor configured to monitor a pressure within a lumen in which the instrument 875 is positioned. The instrument 875 is in communication with an interface 876 via connection 877. In some instances, interface 876 is a hemodynamic monitoring system or other control device, such as Siemens AXIOM Sensis, Mennen Horizon XVu, and Philips Xper IM Physiomonitoring 5. In one particular embodiment, instrument 875 is a pressure-sensing catheter that includes fluid column extending along its length. In such an embodiment, interface 876 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 876. In other instances, the pressure sensor is a separate component positioned between the instrument 875 and the interface 876. The interface 876 is communicatively coupled to the computing device 872 via a connection 878.

Similar to the connections between instrument 852 and the computing device 872, interface 876 and connections 877 and 878 facilitate communication between the one or more sensors, transducers, and/or other monitoring elements of the instrument 875 and the computing device 872. However, this communication pathway is exemplary in nature and should not be considered limiting in any way. In that regard, it is understood that any communication pathway between the instrument 875 and the computing device 872 may be utilized, including physical connections (including electrical, optical, and/or fluid connections), wireless connections, and/or combinations thereof. In that regard, it is understood that the connection 878 is wireless in some instances. In some instances, the connection 878 includes a communication link over a network (e.g., intranet, internet, telecommunications network, and/or other network). In that regard, it is understood that the computing device 872 is positioned remote from an operating area where the instrument 875 is being used in some instances. Having the connection 878 include a connection over a network can facilitate communication between the instrument 875 and the remote computing device 872 regardless of whether the computing device is in an adjacent room, an adjacent building, or in a different state/country. Further, it is understood that the communication pathway between the instrument 875 and the computing device 872 is a secure connection in some instances. Further still, it is understood that, in some instances, the data communicated over one or more portions of the communication pathway between the instrument 875 and the computing device 872 is encrypted.

It is understood that one or more components of the system 850 are not included, are implemented in a different arrangement/order, and/or are replaced with an alternative device/mechanism in other embodiments of the present disclosure. For example, in some instances, the system 850 does not include interface 870 and/or interface 876. In such instances, the connector 868 (or other similar connector in communication with instrument 852 or instrument 875) may plug into a port associated with computing device 872. Alternatively, the instruments 852, 875 may communicate wirelessly with the computing device 872. Generally speaking, the communication pathway between either or both of the instruments 852, 875 and the computing device 872 may have no intermediate nodes (i.e., a direct connection), one intermediate node between the instrument and the computing device, or a plurality of intermediate nodes between the instrument and the computing device. The system 850 can additionally include a bedside interface, such as the bedside interface of medical sensing system 100 (FIG. 1). The bedside interface may be utilized by a clinician to control a instruments 852 and 875 to acquire pressure data during a procedure, watch real-time medical pressure measurements (e.g., visual representations of pressure data, such as pressure waveforms, numerical values, etc.), and interact with the obtained medical sensing data using the bedside interface. In that regard, the bedside interface can be communicatively coupled to the computing device 872, the interfaces 870 and 876, and/or the instruments 864 and 875.

Referring again to FIG. 6, the method 600 begins at block 610 where pressure measurements are obtained using diagnostic instruments such as instruments 830, 832. The diagnostic instruments are also configured to obtain diagnostic information about the vessel 800. In one embodiment, these instruments 830, 320 are sized and shaped to allow positioning of the at least one element configured to monitor pressure within the vessel 800 to be positioned proximal and/or distal of stenosis 808 as necessary based on the configuration of the devices. A variety of sensors may be integrated with this instrument, such as piezo-resistive pressure sensors, piezo-electric pressure sensors, capacitive pressure sensors, electromagnetic pressure sensors, a fluid column, optical pressure sensors, and/or combinations thereof.

In block 620, the pressure measurement data is transmitted to a processing system. This processing system may take the form a computing device 872. In some embodiments, the pressure measurement data may be sent directly to a PIM 112 or interface 870. The transmission of data may be accomplished through a wired connection (using cable 866) or a wireless connection. In that regard, the processing system may be positioned remote from an operating area where the diagnostic instrument is being used. Having the connection 874 include a connection over a network can facilitate communication between the diagnostic instrument and the processing system regardless of whether the computing device is in an adjacent room, an adjacent building, or in a different state/country. In typical embodiments, a processing system may collect raw pressure data from the diagnostic instrument and process the data to render visual representations of the obtained pressure data.

In block 630, data is transmitted to the boom display 122 and bedside interface 202 to facilitate the display of medical imagery. This medical imagery may be diagnostic visualizations and may include numerical, graphical, textual, and/or other suitable visualizations. The bedside interface 202 and boom display 122 retrieve the visual representations from the processing system and displays them to a user in real-time. As discussed above, a PIM 112 or interface 870 may be used in conjunction with a bedside interface 202 to display diagnostic representations to a clinician 107 or patient 106.

In block 640, the bedside interface 202 is used to display a close up region of interest. Specifically, the bedside interface may present pressure measurements or visual representations of the obtained pressure data on the bedside interface and the clinician 107 may navigate through them using gestures on the bedside interface's 202 touch panel. This close up region may show details not apparent in the more general display on the boom display 122, and specified statistical data may accompany this close up display.

In block 650, a clinician 107 analyzes the medical imagery or diagnostic visualization on the beside interface 202. The clinician analyzes the obtained pressure data or visual representations of the obtained pressure data, directly on the bedside interface 202. For example, the user of the bedside interface interacts with the obtained pressure data or visual representations through a series of presses, moves and releases using a finger or stylus on the interface's touch-sensitive display. These actions are interpreted by the bedside interface's 202 internal processor. In some embodiments, the obtained pressure data and/or visual representations can be modified in response to the user touch inputs. For example, a user touch input on the bedside interface 202 can select a specific point of a pressure waveform that corresponds to a specific time at which pressure measurements were obtained. In an another example, where diagnostic instruments take pressure measurements along the length of a vessel 800, a user may be able to check pressure measurements associated with different sections of the vessel. In response to the user touch input, pressure data obtained at the specific time can be displayed proximate the specific point on the pressure waveform on the bedside interface. The clinician 107 may share the visualizations with a patient 106 at this step.

In block 660, a clinician 700 plans a percutaneous coronary intervention based on the analysis with the bedside interface. The bedside interface may be used to place virtual markers on diagnostic visualizations, or to list pressure data to be used on the planning process. Additionally, diagnostic visualizations may be overlaid on images of a vessel displayed on the boom display 122 and/or bedside interface 202. These diagnostic visualizations may assist the clinician 107 in determining the best available treatment options for a particular patient.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system of planning treatment of a vessel of a patient, comprising:
   a processor configured for communication with an intravascular pressure-sensing instrument configured to be positioned within the vessel, wherein the processor is configured to:
   obtain intravascular pressure measurements from the vessel using the intravascular pressure-sensing instrument while the intravascular pressure-sensing instrument is moved through the vessel;
   display, on a first visualization device, a two-dimensional x-ray image of the vessel obtained by an external imaging device;
   receive a first user input directly on the two-dimensional x-ray image, wherein the first user input comprises a selection of a region of interest from the two-dimensional x-ray image;
   display a portion of two-dimensional x-ray image comprising the region of interest on a second visualization device different from the first visualization device, at the same time as the two-dimensional x-ray image is displayed on the first visualization device, wherein the region of interest is magnified on the second visualization device;
   receive a second user input representative of a proposed treatment to position a treatment device in the region of interest; and
   update, in response to the second user input, the second visualization device to include a treatment visualization overlaid on the region of interest, the treatment visualization comprising:
   a first graphical representation of a length of the proposed treatment in the region of interest; and
   a second graphical representation proximate to the first graphical representation, the second graphical representation indicating a simulated change in an intravascular pressure ratio resulting from the proposed treatment, wherein the intravascular pressure ratio is determined based on the obtained intravascular pressure measurements from the region of interest.

2. The system of claim 1, further including the intravascular pressure-sensing instrument.

3. The system of claim 2, wherein the intravascular pressure-sensing instrument comprises at least one of a pressure-sensing catheter or a pressure-sensing guidewire.

4. The system of claim 1, wherein the second visualization device is separate from the first visualization device.

5. The system of claim 1,
wherein the second visualization device comprises a portable touch-screen display device, and
wherein the processor is configured to receive the user input from the portable touch-screen display device.

6. The system of claim 1, wherein the processor is further configured to:
display, on the first visualization device, first diagnostic visualizations based on the obtained intravascular pressure measurements; and
display, on the second visualization device, second diagnostic visualizations based on the obtained intravascular pressure measurements.

7. The system of claim 6, wherein at least one of the first diagnostic visualizations or the second diagnostic visualizations comprises at least one of: the intravascular pressure measurements from the intravascular pressure-sensing instrument or the intravascular pressure ratio of the pressure measurements from the intravascular pressure-sensing instrument.

8. The system of claim 6, wherein at least one of the first diagnostic visualizations or the second diagnostic visualizations comprises at least one of:
an intensity map based on changes in the intravascular pressure ratio; or
a graph of a gradient of the intravascular pressure ratio.

9. The system of claim 6, wherein the second diagnostic visualizations represent a different set of information generated than the first diagnostic visualizations.

10. The system of claim 1, wherein the first graphical representation of the length of the proposed treatment comprises a representation of a stent overlaid on the region of interest, wherein the length of the proposed treatment represents a length of the stent.

11. The system of claim 10, wherein the second graphical representation indicating the simulated change in the pressure ratio comprises a change in the intravascular pressure ratio over the length of the stent.

12. The system of claim 1, wherein the processor is further configured to:
receive a third user input representative of a further proposed treatment;
update, in response to the third user input, the display of the second visualization device to simulate the further proposed treatment, wherein simulating the further proposed treatment includes generating a third graphical representation of the further proposed treatment; and
compare the proposed treatment with the further proposed treatment to identify a recommended treatment.

* * * * *